United States Patent
Martin et al.

(10) Patent No.: US 10,550,064 B2
(45) Date of Patent: Feb. 4, 2020

(54) SEPARATING CARBOXYLIC ACIDS

(71) Applicants: Rohm and Haas Company, Collegeville, PA (US); Dow Global Technologies LLC, Midland, MI (US)

(72) Inventors: Collin H. Martin, North Wales, PA (US); Stephen Pease, Ambler, PA (US); Daryl J. Gisch, Midland, MI (US); Stanislas Baudouin, La Rochelle (FR)

(73) Assignees: ROHM AND HAAS COMPANY, Collegeville, PA (US); DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 15/769,568

(22) PCT Filed: Nov. 1, 2016

(86) PCT No.: PCT/US2016/059894
§ 371 (c)(1),
(2) Date: Apr. 19, 2018

(87) PCT Pub. No.: WO2017/079151
PCT Pub. Date: May 11, 2017

(65) Prior Publication Data
US 2018/0312459 A1 Nov. 1, 2018

Related U.S. Application Data

(60) Provisional application No. 62/251,717, filed on Nov. 6, 2015.

(51) Int. Cl.
| | |
|---|---|
| *C07C 51/47* | (2006.01) |
| *B01D 15/36* | (2006.01) |
| *C07H 3/00* | (2006.01) |
| *B01D 15/34* | (2006.01) |
| *C07H 3/02* | (2006.01) |
| *B01J 20/26* | (2006.01) |
| *B01J 20/28* | (2006.01) |
| *C07C 59/265* | (2006.01) |
| *C07C 55/10* | (2006.01) |
| *C07C 59/08* | (2006.01) |

(52) U.S. Cl.
CPC .............. *C07C 51/47* (2013.01); *B01D 15/34* (2013.01); *B01D 15/363* (2013.01); *B01J 20/26* (2013.01); *B01J 20/28004* (2013.01); *C07H 3/00* (2013.01); *C07H 3/02* (2013.01); *B01J 20/28007* (2013.01); *C07C 55/10* (2013.01); *C07C 59/08* (2013.01); *C07C 59/265* (2013.01)

(58) Field of Classification Search
CPC ......... C07C 51/47; C07C 59/01; C07C 59/08; C07C 59/235; C07C 59/265; C07C 55/10; B01J 20/26; B01J 20/28004; B01J 20/28007; B01D 15/36; B01D 15/363; B01D 15/34; C07H 3/00; C07H 3/02; C07H 1/06
See application file for complete search history.

(56) References Cited

U.S. PATENT DOCUMENTS

| | | |
|---|---|---|
| 2,664,441 A | 12/1953 | Owens |
| 4,851,574 A | 7/1989 | Kulprathipanja |
| 5,068,418 A * | 11/1991 | Kulprathipanja ....... C07C 51/47 562/580 |
| 5,068,419 A * | 11/1991 | Kulprathipanja ....... C07C 51/47 562/580 |
| 5,132,456 A | 7/1992 | King et al. |
| 6,284,904 B1 | 9/2001 | Ponnampalam |
| 7,241,918 B1 | 7/2007 | Kulprathipanja |
| 2013/0345473 A1 | 12/2013 | Archer et al. |

FOREIGN PATENT DOCUMENTS

| | | | |
|---|---|---|---|
| EP | 2 921 471 A1 * | 9/2015 | ............. C07C 51/47 |
| EP | 2921471 A1 | 9/2015 | |

OTHER PUBLICATIONS

EP 2 921 471 A1; Petit, A. et al., Method for Extracting Aconitic acid from products of the sugar cane industry, 2015, English translation; 22 pages (Year: 2015).*
Amberlite IRA458 CI, The Dow Chemical Company, Product data sheet, Form No. 177-03057-0313, 2 pages (Year: 2019).*
Amberlite IRA410 CI, Rohm and Haas, Product data sheet, 2 pages (Year: 2019).*
Lennetech: "Dowex(TM) Marathon(TM) MSA Uniform Particle Size, High Capacity, Macroporous Strong Base Anion Exchange Resin for Water Demineralization Applications" (2015).
Ding, et al., "Simultaneous determination of organic acids and inorganic anions in tea by ion chromatography", J. Chromatogr. A, vol. 764, pp. 341-345 (1997).
Lee, et a., "Separation of Lactic Acid from Acetic Acid Using a Four-Zone SMB", Biotechnol. Prog., vol. 20, pp. 179-192 (2004).
Margarella, et al., "Dissociation of Sulfuric Acid in Aqueous Solution: Determination of the Photoelectron Spectral Fingerprints of H2SO4, HSO4-, and SO42- in Water", J. Phys. Chem. C, vol. 117, pp. 8131-8137 (2013).

* cited by examiner

*Primary Examiner* — Yate' K Cutliff
(74) *Attorney, Agent, or Firm* — Carl P. Hemenway; Kenneth Crimaldi

(57) ABSTRACT

A process of separating carboxylic acids comprising two steps. The first step is to provide an aqueous solution comprising (i) one or more mono-carboxylic acids, (ii) one or more di-carboxylic acids, and (iii) one or more tri-carboxylic acids. The second step is to pass the aqueous solution through a collection of resin particles, where the resin particles comprise covalently bound quaternary ammonium groups, and wherein the collection of resin particles has uniformity coefficient of 1.5 or less.

6 Claims, No Drawings

SEPARATING CARBOXYLIC ACIDS

A variety of processes create complex aqueous solutions of many different solutes, and it is often desired to separate those individual solutes. For example, some fermentation processes result in an aqueous solution that includes various types of carboxylic acids. It is desirable to find a process that separates these carboxylic acids from each other.

U.S. Pat. No. 2,664,441 describes a process in which a solution containing carboxylic acids is poured onto a column of an ion exchange resin, and the column is then washed with water and then eluted with an acidic aqueous solution. It is desired to provide a method using a different resin from that used by U.S. Pat. No. 2,664,441 in order to provide a method that has one or more of the following advantages: is capable of separating carboxylic acids of widely varying pKa values; is capable of separating the carboxylic acids from each other when the concentration of carboxylic acids, prior to separation, is relatively high; and is capable of operating effectively at relatively high elution flow rates.

The following is a statement of the invention.

An aspect of the present invention is a process of separating carboxylic acids comprising
  (a) providing an aqueous solution comprising
    (i) one or more mono-carboxylic acids,
    (ii) one or more di-carboxylic acids, and
    (iii) one or more tri-carboxylic acids, and
  (b) passing the aqueous solution through a collection of resin particles, where the resin particles comprise covalently bound quaternary ammonium groups, and wherein the collection of resin particles has uniformity coefficient of 1.5 or less.

The following is a detailed description of the invention.

As used herein, the following terms have the designated definitions, unless the context clearly indicates otherwise.

Organic compounds are compounds that contain carbon, excluding compounds generally considered to be inorganic. Carbon-containing compounds that are generally considered to be inorganic include the following: binary oxides and sulfides of carbon; ternary metallic cyanides, ternary metallic carbonyls, phosgene, carbonyl sulfide; and metallic carbonates.

As used herein, a mono-carboxylic acid is a compound that has exactly one carboxyl group per molecule; a di-carboxylic acid is a compound that has exactly two carboxyl groups per molecule; and a tri-carboxylic acid is a compound that has exactly three carboxyl groups per molecule. The carboxyl groups may be in the neutral form or in the anion form or a mixture thereof.

A hydroxyl group is an OH group in which the 0 atom of the hydroxyl group is covalently bonded to a carbon atom, and that carbon atom is in turn bonded only to hydrogen atoms or other carbon atoms or a mixture thereof. The OH group that as part of a carboxyl group is not considered to be a hydroxyl group.

"Resin" as used herein is a synonym for "polymer." A "polymer," as used herein is a relatively large molecule made up of the reaction products of smaller chemical repeat units. Polymers may have structures that are linear, branched, star shaped, looped, hyperbranched, crosslinked, or a combination thereof; polymers may have a single type of repeat unit ("homopolymers") or they may have more than one type of repeat unit ("copolymers"). Copolymers may have the various types of repeat units arranged randomly, in sequence, in blocks, in other arrangements, or in any mixture or combination thereof. Polymers have weight-average molecular weight of 2,000 or more.

Molecules that can react with each other to form the repeat units of a polymer are known herein as "monomers." The repeat units so formed are known herein as "polymerized units" of the monomer.

Vinyl monomers have the structure I

where each of $R^1$, $R^2$, $R^3$, and $R^4$ is, independently, a hydrogen, a halogen, an aliphatic group (such as, for example, an alkyl group), a substituted aliphatic group, an aryl group, a substituted aryl group, another substituted or unsubstituted organic group, or any combination thereof. Vinyl monomers have molecular weight of less than 1,000. Vinyl monomers include, for example, styrene, substituted styrenes, dienes, ethylene, ethylene derivatives, and mixtures thereof. Ethylene derivatives include, for example, unsubstituted and substituted versions of the following: vinyl acetate and acrylic monomers. Acrylic monomers are monomers selected from substituted and unsubstituted (meth)acrylonitrile, (meth)acrylic acid, substituted and unsubstituted alkyl esters of (meth)acrylic acid, substituted and unsubstituted amides of (meth)acrylic acid, and mixtures thereof. As used herein, the prefix "(meth)acryl-" means either acryl- or methacryl-. "Substituted" means having at least one attached chemical group such as, for example, alkyl group, alkenyl group, vinyl group, hydroxyl group, alkoxy group, carboxylic acid group, phosphoric acid group, sulfonic acid group, amino group, substituted amino group, other functional groups, and combinations thereof.

As used herein, vinyl aromatic monomers are vinyl monomers in which one or more of $R^1$, $R^2$, $R^3$, and $R^4$ contain one or more aromatic ring.

A monovinyl monomer is a vinyl monomer that has exactly one non-aromatic carbon-carbon double bond per molecule. A multivinyl monomer is a vinyl monomer that has two or more non-aromatic carbon-carbon double bonds per molecule.

A vinyl polymer is a polymer in which 90% or more of the polymerized units, by weight based on the weight of the polymer, are polymerized units of one or more vinyl monomers. An acrylic polymer is a vinyl polymer in which 50% or more of the polymerized units, by weight based on the weight of the polymer, are acrylic monomers.

A collection of particles is characterized by the diameters of the particles. If a particle is not spherical, the diameter of the particle is considered to be the diameter of a particle having the same volume as the particle. A collection of particles is characterized herein by the parameters D10, D50, and D60. D10 is the value such that exactly 10% of the collection of particles by volume have diameter of D10 or less. D50 is the value such that exactly 50% of the collection of particles by volume have diameter of D50 or less. D60 is the value such that exactly 60% of the collection of particles by volume have diameter of D60 or less. The parameters D10, D50, and D60 are determined by mixing a sample of the collection of particles into water to form a dilute slurry and using laser light scattering to determine D10, D50, and D60.

A collection of particles may also be characterized by the uniformity coefficient (UC), which is defined herein as UC=D60/D10.

The collection of resin particles occupies a total volume of space that includes the resin particles and also includes the interstitial volumes that are present in between adjacent resin particles. This total volume is known herein as the bed volume (BV). The bed volume is larger than the total volume of the resin particles, which only includes the volumes of the resin particles themselves and not the interstitial volumes.

Some resin particles are macroporous, which means that the particles have pores with an average pore diameter of 50 nm or larger. Pore diameter is determined by the Brunauer-Emmett-Teller (BET) method. Resin particles that have no pores or that have pores of average diameter less than 50 nm are gel resin particles.

As used herein, the term sugar refers to a monosaccharide, a mixture of monosaccharides, a disaccharide, a mixture of disaccharides, or a mixture of one or more monosaccharides with one or more disaccharides.

A quaternary ammonium group has the structure II:

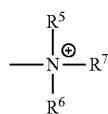

where each of $R^5$, $R^6$, and $R^7$ is, independently, a substituted or unsubstituted alkyl group; and where the dangling bond at the left side of structure II represents a covalent bond between the nitrogen atom in structure II and a carbon atom that is covalently bonded to the resin particles. Also present in the composition will be anions of sufficient charge and quantity to balance the cations shown in structure II.

The present invention involves the use of a collection of resin particles. Preferably the portion of the collection of resin particles in which the resin particles all have the same composition as each other is, by weight based on the dry weight of the entire collection of resin particles, 50% or more; more preferably 75% or more; more preferably 90% or more; more preferably 95% or more.

Preferably the resin particles comprise polymerized units of one or more monovinyl monomer and polymerized units of one or more multivinyl monomer. Preferred monovinyl monomers are monovinyl vinyl aromatic monomers, monovinyl acrylic monomers, and mixtures thereof; more preferred are monovinyl aromatic monomers; more preferred is styrene. Preferred multivinyl monomers are divinylbenzene, allyl (meth)acrylate, monomers having two or more (meth)acrylate groups, and mixtures thereof; more preferred is divinylbenzene.

The resin particles used in the present invention have covalently bound quaternary ammonium groups of structure II as defined above. Preferably, each of $R^5$, $R^6$, and $R^7$ is independently selected from unsubstituted alkyl groups and alkyl groups substituted with a hydroxyl group and no other substituents. Preferably, $R^5$ is an unsubstituted alkyl group having 1 to 8 carbon atoms; more preferably 1 to 4 carbon atoms; more preferably 1 or 2 carbon atoms; more preferably 1 carbon atom. Preferably, $R^6$ is an unsubstituted alkyl group having 1 to 8 carbon atoms; more preferably 1 to 4 carbon atoms; more preferably 1 or 2 carbon atoms; more preferably 1 carbon atom. Preferably, $R^7$ is either an unsubstituted alkyl group or an alkyl group substituted with exactly one hydroxyl group and having no other substitutions. Preferably, $R^7$ has 1 to 8 carbon atoms; more preferably 1 to 4 carbon atoms; more preferably 1 or 2 carbon atoms. Preferably, if $R^7$ has a hydroxyl group, then $R^7$ has two carbon atoms. Preferably, if $R^7$ has a hydroxyl group, then $R^7$ has 2 carbon atoms.

The quaternary ammonium functional groups may be introduced by any method. For example (method I), the quaternary ammonium functional group may be covalently bound to a monomer prior to the polymerization process that forms the resin, with the polymerization process conducted in a way that preserves the quaternary ammonium functional group. Preferably (method II), quaternary ammonium functional groups are attached to the resin by conducting one or more chemical reactions after the polymerization process that formed the resin is complete.

The collection of resin particles also contains anions, in quantity and charge sufficient to balance the total charge of the quaternary ammonium groups covalently bound to the resin particles. Preferably, these anions are not covalently bound to the resin particles.

To characterize the amounts of polymerized units of particular monomers that are present in a resin, the following procedure is used. It is imagined that all of the quaternary ammonium functional groups are replaced by hydrogen atoms to form an imaginary polymer, and the weight % of polymerized units of a particular monomer is determined for the imaginary polymer, and that weight % is used to characterize the actual finished polymer. This procedure is easy to envision for resins made by method II defined above. The polymerization is conducted to form a copolymer, and the weight % of each type of monomer, based on the weight of that copolymer, is characterized. After the chemical reaction is conducted to introduce quaternary ammonium functional groups, the finished resin, bearing quaternary ammonium functional groups, is still described by the weight % figures that were determined for the copolymer prior to the introduction of the quaternary ammonium functional groups. For example, a copolymer could be made using 97% by weight styrene and 3% by weight divinylbenzene, based on the total weight of monomers. The resulting copolymer would have 97% by weight polymerized units of styrene and 3% by weight polymerized units of divinylbenzene. After the copolymer was subjected to one or more chemical reactions to introduce quaternary ammonium groups, the resulting resin would still be described as having 3% polymerized units of divinylbenzene.

Preferably, the amount of polymerized units of multivinyl monomer in the resin is, by weight based on the dry weight of the resin, 0.5% or more; more preferably 1% or more. Preferably, the amount of polymerized units of multivinyl monomer in the resin is, by weight based on the dry weight of the resin, 10% or less; more preferably 8% or less.

Preferably, the sum of the weight % of polymerized units of multivinyl monomer plus the weight % of polymerized units of monovinyl monomer, based on the dry weight of the resin, is 80% or more; more preferably 90% or more; more preferably 95% or more; more preferably 98% or more.

Preferably, the amount of polymerized units of vinyl aromatic monomer in the resin is, by weight based on the weight of the resin, 25% or more; more preferably 50% or more; more preferably 75% or more; more preferably 90% or more; more preferably 95% or more; more preferably 99% or more.

It is useful to characterize the resin particles immediately before contact with the aqueous solution. At that time, the quantity of anions in the resin that are either sulfate or chloride is preferably 50 mole % or more; more preferably 75 mole % or more; more preferably 90 mole % or more. Sulfate anions are preferred over chloride anions. As used herein, the term "sulfate anion" includes both the sulfate anion $SO_4^{-2}$ and the bisulfate anion $HSO_4^{-1}$. More preferably, at that time, the quantity of anions in the resin that are sulfate is 50 mole % or more; more preferably 75 mole % or more; more preferably 90 mole % or more.

The resin particles may be either gel resin particles or macroporous resin particles. Preferred are gel resin particles.

Resins having quaternary ammonium functional groups are characterized by the total capacity of the resin. Total capacity is measured using ASTM Method D2187-95, procedure H (ASTM International, West Conshohocken, Pa., USA), reported in units of equivalents per liter of resin (eq/L). Preferably the resin used in the present invention has total capacity of 2.5 eq/L or less; more preferably 2 eq/L or less. Preferably the resin used in the present invention has total capacity of 0.5 eq/L or more; more preferably 0.8 eq/L or more.

The resin is present as a collection of resin particles. Preferably the collection of resin particles has D50 of 500 μm or less; more preferably 400 μm or less; more preferably 350 μm or less. Preferably the collection of resin particles has D50 of 100 μm or more; more preferably 150 μm or more; more preferably 200 μm or more; more preferably 250 μm or more. Preferably UC of the collection of particles is 1.5 or lower; more preferably 1.4 or lower; more preferably 1.3 or lower; more preferably 1.2 or lower.

The present invention involves the use of an aqueous solution. The aqueous solution contains one or more mono-carboxylic acid. Preferred mono-carboxylic acids have no atoms other than carbon, hydrogen, and oxygen. Preferred mono-carboxylic acids have 8 or fewer carbon atoms; more preferably 6 or fewer; more preferably 4 or fewer. Preferred mono-carboxylic acids have a hydroxyl group. A preferred mono-carboxylic acid is lactic acid.

The aqueous solution contains one or more di-carboxylic acid. Preferred di-carboxylic acids have no atoms other than carbon, hydrogen, and oxygen. Preferred di-carboxylic acids have 10 or fewer carbon atoms; more preferably 8 or fewer; more preferably 6 or fewer. Preferred di-carboxylic acids have no hydroxyl group. A preferred di-carboxylic acid is succinic acid.

The present invention involves the use of an aqueous solution. The aqueous solution contains one or more tri-carboxylic acid. Preferred tri-carboxylic acids have no atoms other than carbon, hydrogen, and oxygen. Preferred tri-carboxylic acids have 12 or fewer carbon atoms; more preferably 10 or fewer; more preferably 8 or fewer. Preferred tri-carboxylic acids have 4 or more carbon atoms; more preferably 5 or more. Preferred tri-carboxylic acids have a hydroxyl group. A preferred tri-carboxylic acid is citric acid.

Each carboxylic acid has a characteristic pKa value. For dicarboxylic acids and tri-carboxylic acids, the characteristic pKa of the compound is considered herein to be the lowest pKa value. Preferably, one or more carboxylic acids are present that have pKa less than or equal to 3.5. Preferably, one or more carboxylic acids are present that have pKa more than 3.5. The aqueous solution may be characterized by delta-pKa=pKamax−pKamin, where pKamax is the pKa value of the carboxylic acid having the highest pKa value of all the carboxylic acids present in the aqueous solution, and pKamin is the pKa value of the carboxylic acid having the lowest pKa value of all the carboxylic acids present in the aqueous solution. Preferably, delta-pKa is 0.6 or more; more preferably 0.8 or more; more preferably 1 or more. Preferably, delta-pKa is 5 or less.

In the practice of the present invention, the aqueous solution is passed through a collection of resin particles. It is contemplated that the interaction between the resin particles and the various carboxylic acids will be different for each of the carboxylic acids. Therefore it is contemplated that each carboxylic acid in the aqueous solution will pass through the collection of resin particles at its own characteristic rate. Consequently some of the carboxylic acids will exit the collection of resin particles sooner than others. Thus the process of the present invention will serve to separate the various carboxylic acids dissolved in the aqueous solution from each other.

Preferably, the pH of the aqueous solution is 6 or less; more preferably 5 or less; more preferably 4 or less; more preferably 3 or less; more preferably 2 or less; more preferably 1.85 or less.

Preferably the aqueous solution also contains one or more sugar. Preferred sugar is glucose. Preferably the amount of glucose in the aqueous solution is, by weight based on the weight of the aqueous solution, 0.5% or more; more preferably 1% or more; more preferably 2% or more. Preferably the amount of glucose in the aqueous solution is, by weight based on the weight of the aqueous solution, 20% or less.

Preferably, the process of the present invention also separates each of the sugars dissolved in the aqueous solution from all of the carboxylic acids dissolved in the aqueous solution.

The present invention involves passing the aqueous solution through a collection of resin particles. The collection of resin particles is preferably contained in a vessel. Preferably, the vessel prevents the collection of particles from escaping the vessel and also allows aqueous solution to enter the vessel, to pass through the collection of resin particles, and to exit the vessel.

Preferably, the process of the aqueous solution passing through the collection of resin particles involves contact between the aqueous solution and resin particles. Preferably, the collection of resin particles is contained in a vessel, and while the aqueous solution is passing through the collection of resin particles, 50% or more of the resin particles by volume, based on the volume of the collection of resin particles, are in contact only with other resin particles, the aqueous solution, the interior surface of the vessel, or a combination thereof.

Preferably, the vessel containing the collection of resin particles is a column. A column has an inlet for the aqueous solution and an outlet for the aqueous solution. Preferably, the outlet is located opposite to the inlet. The line from the inlet to the outlet determines the "length" dimension of the vessel. Preferably, the length of the interior of the vessel is greater than any dimension of the interior of the vessel that is perpendicular to the length. A planar slice of the interior of the vessel taken perpendicular to the length is a cross section. Preferably, the cross section is the same over 90% or more of the length of the vessel. Preferred cross section is circular. A preferred category of vessels are columns suitable for use in chromatography.

It is useful to characterize the collection of resin particles as it exists immediately prior to the introduction of the aqueous solution onto the collection of resin particles. Preferably, the ionic form of the resin particles is the same throughout the collection of resin particles. Preferably, the resin particles are packed together with liquid in contact with the resin particles, resident in the voids between particles. Preferably, the pH of the liquid in contact with the resin particles is the same throughout the collection of resin particles. Preferably, that pH is 3 or less; more preferably 2 or less; more preferably 1.85 or less.

Preferably, the aqueous solution is forced into the inlet of the vessel, passes through the collection of resin particles, and passes out of the vessel through the outlet due to pressure. The pressure may be caused by gravity or by a mechanical device such as a pump.

Preferably, all of the compounds dissolved in the aqueous solution will be carried through the collection of resin particles and will exit the vessel through the outlet. It is contemplated that each dissolved compound will be retarded in its passage through the collection of resin particles due to interaction of the dissolved compound with the resin particles. Preferably, each dissolved compound will be retarded to a unique extent that is characteristic of that compound.

Two preferred embodiments are "pulse embodiments" and "SMB embodiments."

In pulse embodiments, a preliminary aqueous solution is provided. The preliminary aqueous solution preferably has all the required and preferred characteristics of the aqueous solution of the present invention as described above.

Preferably, the concentration of mono-carboxylic acid in the preliminary aqueous solution is, by weight based on the weight of the preliminary aqueous solution, 0.1% or higher; more preferably 0.2% or higher; more preferably 0.5% or higher; more preferably 1% or higher; more preferably 2% or higher. Preferably, the concentration of mono-carboxylic acid in the preliminary aqueous solution is, by weight based on the weight of the preliminary aqueous solution, 50% or lower; more preferably 30% or lower.

Preferably, the concentration of di-carboxylic acid in the preliminary aqueous solution is, by weight based on the weight of the preliminary aqueous solution, 0.1% or higher; more preferably 0.2% or higher; more preferably 0.5% or higher; more preferably 1% or higher; more preferably 2% or higher. Preferably, the concentration of di-carboxylic acid in the preliminary aqueous solution is, by weight based on the weight of the preliminary aqueous solution, 50% or lower; more preferably 30% or lower.

Preferably, the concentration of tri-carboxylic acid in the preliminary aqueous solution is, by weight based on the weight of the preliminary aqueous solution, 0.1% or higher; more preferably 0.2% or higher; more preferably 0.5% or higher; more preferably 1% or higher; more preferably 2% or higher. Preferably, the concentration of tri-carboxylic acid in the preliminary aqueous solution is, by weight based on the weight of the preliminary aqueous solution, 50% or lower; more preferably 30% or lower.

In pulse embodiments, a fixed amount of preliminary aqueous solution is added to the vessel through the inlet of the vessel. Preferably, the amount of preliminary aqueous solution is 0.01 BV or more; more preferably 0.02 BV or more; more preferably 0.03 BV or more; more preferably 0.04 BV or more. Preferably, the amount of preliminary aqueous solution is 0.5 BV or less; more preferably 0.2 BV or less; more preferably 0.1 BV or less. Then, a fluid known as the eluent is added continuously to the vessel through the inlet, causing fluid to pass through the collection of resin particles and to exit the vessel through the outlet. The fluid exiting the vessel is collected and analyzed. For each of the carboxylic acids present in the preliminary solution, there is preferably a time period during which the fluid exiting the vessel contains that specific carboxylic acid and either contains no amount of any of the other carboxylic acids that were present in the preliminary solution or else contains a negligible amount of any of the other carboxylic acids that were present in the preliminary solution.

The term "negligible amount" is determined as follows. Two compounds C1 and C2 that are present in the preliminary aqueous solution have an initial weight quotient of $$Q0=(WC10)/(WC20)$$

where WC10=(concentration of C1 in grams per liter in the preliminary aqueous solution), and WC20=(concentration of C2 in grams per liter in the preliminary aqueous solution). The fluid exiting the vessel at some specific time T will have a weight quotient $$QT=(WC1T)/(WC2T)$$

where WC1T=(concentration of C1 in grams per liter in the exiting aqueous solution at time T), and WC2T=(concentration of C2 in grams per liter in the exiting aqueous solution at time T). Then, if the fluid exiting the vessel at time T contains C1, the amount of C2 is considered negligible at time T if QT is equal to or greater than 100*Q0.

Preferably, in a pulse embodiment, the eluent is an aqueous solution having pH of 5 or lower; more preferably 4 or lower; more preferably 3 or lower; more preferably 2 or lower. Preferably, the eluent is a solution of one or more inorganic acid in water. Preferably, the eluent contains 0 to 0.01% of any compound other than inorganic acid and water. Preferred inorganic acids for use in the eluent are hydrochloric acid, sulfuric acid, and mixtures thereof; more preferred is sulfuric acid. Preferably, the eluent is a solution of one or more inorganic acids in water. When the eluent is a solution of one or more inorganic acids in water, preferably the total concentration of inorganic acid is 10 g/L or less; more preferably 5 g/L or less; more preferably 3 g/L or less. When the eluent is a solution of one or more inorganic acids in water, preferably the total concentration of inorganic acid is 0.1 g/L or more.

In pulse embodiments, the preferred flow rate of eluent is 0.2 BV per hour or higher; more preferably 0.5 BV per hour or higher; more preferably 0.9 BV per hour or higher. In pulse embodiments, the preferred flow rate of eluent is 10 BV per hour or less; more preferably 8 BV per hour or less; more preferably 6 BV per hour or less; more preferably 4 BV per hour or lower.

Another method of characterizing the flow rate of eluent is in units of volume per minute per unit area of the cross section of the vessel. Preferably the flow rate of eluent is, in $mL/cm^2/min$, is 0.2 or higher; more preferably 0.5 or higher; more preferably 1 or higher; more preferably 1.5 or higher. Preferably the flow rate of eluent, in $mL/cm^2/min$, is 12 or less; more preferably 10 or less; more preferably 8 or less.

In some procedures outside the practice of the present invention, a preliminary aqueous solution containing certain solutes may be placed onto the top of a column, and then pure water may be eluted through the column, and then an acidic eluent may be eluted through the column. Preferably, in the practice of the present invention, no pure water is introduced into the column in between the introduction of the preliminary aqueous solution and the beginning of elution with the eluent.

Preferred are SMB embodiments, which involve the use of a simulated moving bed (SMB). SMB methods are known, as explained for example by M. Juza, et. al, in "Simulated moving-bed chromatography and its application to chirotechnology," *Trends in Biotechnology*, volume 18, pages 108-118, March 2000. The following is a brief description of an SMB method for separating a solution containing two solutes, one which elutes relatively slowly and one which elutes relatively quickly. It is contemplated that, in the present invention, additional inlets and/or outlets could be added to the SMB method to remove additional solutes.

In a simulated moving bed method, a plurality of identical columns is arrayed in a continuous loop. Eluent passes under pressure through the loop in one direction, the "downstream" direction. Valves and pipes are arranged so that inlet and outlet points are periodically moved from one point in the loop to the next in the downstream direction, at a rate in between the rates R1 and R2, where R1 is the rate of progress through the column of slower-eluting species, and R2 is the rate of progress through the column of faster-eluting species. The inlet apparatus uses pipes and valves to introduce preliminary aqueous solution into the loop. An outlet apparatus is located upstream of the inlet apparatus; this outlet apparatus uses pipes and valves to remove eluent that is relatively rich in slower-eluting dissolved species from the loop. A second outlet apparatus is located downstream of the inlet apparatus; this outlet apparatus uses pipes and valves to remove eluent that is relatively rich in faster-eluting dissolved species from the loop.

For SMB embodiments, the required and preferred features of the preliminary aqueous solution are the same as described above for the preliminary aqueous solution used in pulse embodiments. For SMB embodiments, the required and preferred features of the eluent are the same as described above for the eluent used in pulse embodiments. For SMB embodiments, the preferred flow rate is the same as for pulse embodiments as described above.

Preferably, the method of the present invention is conducted at a temperature of 20° C. or higher; more preferably 25° C. or higher; more preferably 30° C. or higher; more preferably 35° C. or higher; more preferably 40° C. or higher. Preferably, the method of the present invention is conducted at a temperature of 80° C. or lower; more preferably 70° C. or lower.

The following are examples of the present invention.

Pulse tests were conducted as follows.

The column was 1000 mm long, 25 mm diameter, with resin bed volume approximately 460 mL. The column had a jacket for temperature control, maintained at 60° C. The loading of resin was done in a column half filled with degassed demineralized water added with 2 g/L of sulfuric acid in water at 60° C. The resin slurry was maintained at the same temperature, and poured in the column while water was extracted at the outlet of the column. The column was loaded up to the top, the adjustable piston was set in place and gently tight on the column to press the resin between two fits and avoid void volume on top.

Eluent was a solution of sulfuric acid in water, at 2 g/L, maintained at 60° C. prior to introduction onto the column. The fractions were collected at the bottom of the column with a constant interval of volume (each 0.04 BV from 0.3 BV to 3 BV; depending on product affinity). The 0.3 first BV contained only eluent and were discarded. At the outlet of the column, 40 to 80 exit samples were recovered, numbered from 1 to "imax," and analyzed. Concentration of solutes in the collected exit samples was determined by HPLC.

For each solute, 20 mL of a preliminary aqueous solution was prepared that contained a single solute at 50 g/L in water. The preliminary aqueous solution and the eluent were both fed to the column at 8 mL/min until the preliminary aqueous solution was all fed to the column, and the eluent continued to be fed at 8 mL/min each until the process was completed.

For each solute, the collected exit samples create a plot of solute concentration versus sample number. Each such plot was analyzed as follows:

$$RV = \sum_i c_i * bv_i * d(bv) \bigg/ \sum_i c_i * d(bv) \qquad \text{equ. 1}$$

and $$(\sigma)^2 = (NUM/DENOM) - RV^2 \qquad \text{equ. 2}$$

where $$NUM = \sum_i c_i * (bv_i)^2 * d(bv)$$

and $$DENOM = \sum_i c_i * d(bv)$$

$$R_{A/B} = (RV_B - RV_A)/(2[\sigma_A + \sigma_B]) \qquad \text{equ. 3}$$

where
bv=eluted volume per unit of BV
RV=average retention volume for the solute per unit of BV
$\sigma^2$=variance of the peak
$\sigma$=square root of $\sigma^2$
c=concentration
i=number of exit sample
d(bv)=sampling interval, per unit of BV
$R_{A/B}$=chromatographic resolution between solute "A" and solute "B"

After each solute is tested, RV and $\sigma^2$ were calculated for that individual solute, using equations 1 and 2 above. Then, the resolution for any pair of solutes is calculated using equation 3 above.

Various resins were tested, as follows:

| Resin | Comparative CR1 | Comparative CR2 | Comparative CR3 | Example R4 |
|---|---|---|---|---|
| Composition type | Acrylic gel | Styrenic[3] gel | Styrenic[3] Macroporous | Styrenic[3] gel |
| Functional Group | tertiary amine | sulfonic acid | None | quaternary amine |
| D50 (μm) | 400 to 500[1] | 310 | 600 to 700[1] | 310 |
| UC[2] | <1.3 | <1.3 | <2.1 | <1.3 |
| Total Capacity (eq/L) | 1.6 | 1.6 | not applicable | 1.3 |

[1]harmonic mean size
[2]UC = Uniformity coefficient = D60/D10
[3]Copolymer of Styrene and divinylbenzene; the amount of polymerized units of divinylbenzene was between 2% and 8% by weight based on the weight of the resin.
CR1 = AMBERLITE ™ CR5550 resin, from the Dow Chemical Company
CR2 = DOWEX ™ MONOSPHERE 99Ca/310 resin, from the Dow Chemical Company
CR3 = AMBERLITE ™ FPX66 resin, from the Dow Chemical Company Results were as follows:
Results for the individual pulse tests were as follows:

| Item | Solute | CR1 | CR2 | CR3 | R4 |
|---|---|---|---|---|---|
| RV | glucose | 0.69 | 0.64 | 0.83 | 0.74 |
| RV | citric acid | 1.32 | 0.64 | 1.23 | 2.83 |
| RV | lactic acid | 0.80 | 0.90 | 1.27 | 1.29 |
| RV | succinic acid | 1.00 | 0.76 | 1.74 | 1.97 |

The calculated Resolution values for each pair of solutes were as follows:

| Item | Solute A | Solute B | CR1 | CR2 | CR3 | R4 |
|---|---|---|---|---|---|---|
| $R_{A/B}$ | glucose | citric acid | 1.34 | 0.01 | 0.87 | 2.89 |
| $R_{A/B}$ | glucose | lactic acid | 0.34 | 0.88 | 1.01 | 0.84 |
| $R_{A/B}$ | glucose | succinic acid | 0.88 | 0.46 | 1.56 | 2.46 |
| $R_{A/B}$ | citric acid | lactic acid | 1.01 | 0.84 | 0.09 | 1.49 |
| $R_{A/B}$ | citric acid | succinic acid | 0.59 | 0.44 | 0.79 | 0.97 |
| $R_{A/B}$ | lactic acid | succinic acid | 0.50 | 0.44 | 0.74 | 0.84 |

When comparative resin CR1 was used, the elution curve for succinic acid strongly overlapped those of citric acid and lactic acid, as shown by the low values of resolution (less than 0.6) for citric/succinic and for lactic/succinic. When comparative resin CR2 was used, the elution curve for succinic acid strongly overlapped those of citric acid and lactic acid, as shown by the low values of resolution (less than 0.5) for citric/succinic and for lactic/succinic. When comparative resin CR3 was used, citric acid and lactic acid eluted at nearly the same time, as shown by the close RV values, and the resolution between citric acid and lactic acid was low, as shown by the low value $R_{A/B}$ (less than 0.1) for this pair of solutes. When example resin R4 was used, the peaks were all well separated, as shown by the varying values of RV for the various solutes, and the elutions of the solutes were well resolved from each other, as shown by the uniformly high values (all above 0.8) of $R_{A/B}$.

It is contemplated that the results of these pulse procedures using individual solutes show that any mixture of the solutes would be well separated if the mixture were subjected to a pulse procedure. Furthermore, it is contemplated that the good separation in a pulse procedure demonstrates that an SMB method could be readily constructed that would provide good separation among all the solutes.

The invention claimed is:

1. A process of separating carboxylic acids from each other and from monosaccharides comprising
    (a) providing an aqueous solution comprising
        (i) one or more mono-carboxylic acids,
        (ii) one or more di-carboxylic acids,
        (iii) one or more tri-carboxylic acids, and
        (iv) one or more monosaccharides, and
    (b) passing the aqueous solution through a collection of gel resin particles, where the gel resin particles comprise at least 90 wt % polymerized units of styrene, from 1 to 10 wt % polymerized units of multivinyl monomer and covalently bound quaternary ammonium groups, wherein the collection of gel resin particles has uniformity coefficient of 1.3 or less and volume-average diameter of 500 µm or less, and wherein the aqueous solution is passed through the gel resin particles in a vessel in one of two ways: (1) a fixed amount of the aqueous solution is added to the vessel, followed by adding continuously an eluent fluid, with collection and analysis of fluid exiting the vessel, or (2) the vessel is one of a plurality of vessels operated in a simulated moving bed method.

2. The process of claim 1, wherein the aqueous solution comprises glucose.

3. The process of claim 2, wherein the collection of gel resin particles has volume-average diameter of 400 µm or less.

4. The process of claim 3, wherein the collection of gel resin particles comprises anions, and wherein 75 mole % or more of the anions are sulfate.

5. The process of claim 4, wherein the eluent is a solution of one or more inorganic acids in water, wherein total concentration of inorganic acid is 5 g/L or less, and wherein total concentration of inorganic acid is 0.1 g/L or more.

6. The process of claim 5, wherein each of said one or more mono-carboxylic acids has no more than 6 carbon atoms, wherein each of said one or more di-carboxylic acids has no more than 8 carbon atoms, and wherein each of said one or more tri-carboxylic acids has no more than 8 carbon atoms.

\* \* \* \* \*